United States Patent [19]

Haubennestel et al.

[11] Patent Number: 5,130,463

[45] Date of Patent: Jul. 14, 1992

[54] PHOSPHORIC ACID ESTERS, METHOD OF PRODUCING THEM, AND USE THEREOF AS DISPERSANTS

[75] Inventors: Karl-Heinz Haubennestel; Wolfgang Pritschins, both of Wesel, Fed. Rep. of Germany

[73] Assignee: BYK-Chemie, GmbH, Wesel, Fed. Rep. of Germany

[21] Appl. No.: 562,847

[22] Filed: Aug. 6, 1990

[30] Foreign Application Priority Data

Sep. 14, 1989 [DE] Fed. Rep. of Germany ....... 3930687

[51] Int. Cl.$^5$ ................................................. C07F 9/09
[52] U.S. Cl. ................................... 558/172; 558/179; 558/180
[58] Field of Search .......................... 558/172, 179, 180

[56] References Cited

U.S. PATENT DOCUMENTS

| | | | |
|---|---|---|---|
| 2,026,785 | 1/1936 | Harris | 558/179 |
| 3,945,954 | 3/1976 | Batorewicz | 260/2.5 AR |
| 4,183,766 | 1/1980 | Woodward | 106/213 |
| 4,258,448 | 3/1981 | Reitz et al. | 8/582 |
| 4,456,485 | 6/1984 | Iyengar | 106/288 |
| 4,647,647 | 3/1987 | Haubennestel et al. | 528/83 |
| 4,698,099 | 10/1987 | Nakamura et al. | 106/288 |
| 4,717,424 | 1/1988 | Wilfinger et al. | 106/308 |
| 4,720,514 | 1/1988 | Needham | 523/351 |
| 4,746,462 | 5/1988 | Nakamura et al. | 260/403 |
| 4,762,752 | 8/1988 | Haubennestel et al. | 428/407 |
| 4,777,195 | 10/1988 | Hesse et al. | 523/461 |
| 4,795,796 | 1/1989 | Haubennestel et al. | 528/28 |

FOREIGN PATENT DOCUMENTS 193019 9/1986 European Pat. Off. .

OTHER PUBLICATIONS

P. F. Bruins, "Unsaturated Polyester Technology", Gordon and Breach Science Publishers, pp. 211-238 (1976).

Saul Patai, "The Chemistry of Cyanates and Their Derivatives," Part I, Chapter 5 (1977).

Primary Examiner—Mary C. Lee
Assistant Examiner—Michael G. Ambrose
Attorney, Agent, or Firm—Foley & Lardner

[57] ABSTRACT

Phosphoric acid esters and their salts corresponding to the formula (I):

$$(OH)_{3-n}-\overset{\overset{\displaystyle O}{\|}}{P}-(O-R)_n \qquad (I)$$

wherein R represents an aliphatic, cycloaliphatic and/or aromatic moiety having no Zerewitinoff hydrogen, containing at least one ether oxygen atom (—O—) and at least one carboxylic acid ester group (—COO—) and/or urethane group (—NHCOO—), and having an average molecular weight $\overline{M}_n$ of 200 to 10,000, wherein the hydrogen atoms may be partially replaced by halogen atoms, and wherein the ratio of the number of ether oxygen atoms to the number of the carboxylic acid ester groups and/or urethane groups in the molecule (or in every group R) is in the range from 1:20 to 20:1, and n represents 1 or 2. A method for preparing such phosphoric acid esters and salts and the use of such phosphoric acid esters or salts as dispersants or dispersing aids is also disclosed.

12 Claims, No Drawings

PHOSPHORIC ACID ESTERS, METHOD OF PRODUCING THEM, AND USE THEREOF AS DISPERSANTS

BACKGROUND OF THE INVENTION

This invention relates to phosphoric acid esters and their salts, to paints and molding compositions containing them, to the use of these phosphoric acid esters and salts as dispersants, and to solids coated therewith.

High mechanical forces are needed in order to incorporate solids into liquid media. To reduce these dispersing forces it is common to use dispersants which facilitate incorporation of the solids into the medium. These are generally surface active substances, also called tensides, having an anionic, cationic or non-ionic structures. These substances are either applied directly to the solid in small amounts, or they are added to the dispersing medium. The difficulty of dispersion is reduced by such a tenside. It is furthermore known that such solids can tend to reagglomerate after the dispersing process due to mutual forces of attraction, which nullifies the previously expended dispersing efforts and leads to problems.

Unsatisfactory dispersion manifests itself in an increase in viscosity in liquid systems, loss of gloss and changes of color in paints and coatings, unsatisfactory coloring power in pigmented molding compositions, and reduction of mechanical strength in reinforced plastics.

Also, an important factor is the high viscosity of liquid systems having a high solids content. To operate economically, an attempt is made to keep the solids content of such solid-containing dispersions as high as possible in the dispersion, combined with the lowest possible viscosity of the system that is to be dispersed. This is of particular importance in liquid synthetic resin systems, such as unsaturated polyester resins, for example, in which a very low initial working viscosity is desired with the highest possible solids content.

Phosphoric acid esters having various structures have been disclosed, for example, for dispersing or treating pigments. U.S. Pat. No. 4,456,485 describes acidic or neutral phosphoric acid esters of fatty alcohols and alkoxylated fatty alcohols as agents for treating specific blue pigments (alkali blue). Likewise, European Patent Application No. EP 256,427 describes the use of previously known phosphoric acid esters of alkoxylated fatty alcohols for preparing pigment dispersions suitable for aqueous applications. U.S. Pat. No. 4,720,514 describes pigment dispersions made using phosphoric acid esters of alkoxylates having various structures. German Patent Application No. DE 2,726,854 describes phosphoric acid esters of polyols used as dispersants in aqueous media or as detergent builders. These phosphoric acid esters are of a very complex nature and also contain free hydroxyl groups which originate from the epoxides that are used. They are evidently of a polyvalent nature with respect to the free phosphoric acid groups present in the molecules. U.S. Pat. No. 4,717,424 starts from carboxyl group containing phosphoric acid esters which in addition to the phosphoric acid group contain a free -COOH group in the molecule. These are not polymers. These products are used for stabilizing metal pigments against attack by water. U.S. Pat. No. 4,698,099 describes pigment dispersions containing phosphoric acid esters of monohydroxy-terminated polyesters as dispersants.

In may cases, good results can be obtained with the phosphoric acid esters described above. However, these compounds are not widely usable in modern binding resins and plastic systems, such as for example in high-solids paints, aqueous paints, systems which can be hardened by ultraviolet and electron beams, or LS-SMC or LP-SMC molding compositions (low-shrink or low-profile sheet molding compositions).

In a number of different systems, these compounds are not sufficiently compatible. This leads to inadequate dispersion due to insufficient interaction with the surrounding medium, and in many cases to precipitation phenomena and the associated dulling, spotting and increased viscosity.

SUMMARY OF THE INVENTION

It is the object of the present invention to provide dispersants which will not be subject, or will be substantially less subject, to the foregoing disadvantages.

Another object of the invention is to provide dispersants which will be broadly useful both in organic systems and in aqueous systems.

A further object of the invention is to provide dispersants which will make it possible to incorporate very high percentages of solids in liquid organic or aqueous systems while achieving a very low viscosity of the overall system.

These and other objects of the invention are achieved by providing a phosphoric acid ester corresponding to the formula (I)

wherein
R represents an aliphatic, cycloaliphatic and/or aromatic moiety free of any Zerewitinoff hydrogen, containing at least one ether oxygen atom (—O—) and at least one carboxylic acid ester group (—COO—) or urethane group (—NHCOO—), and having an average molecular weight $\overline{M}_n$ of 200 to 10,000, in which aliphatic hydrogen atoms may be partially replaced by halogen atoms, and in which the ratio of the number of ether oxygen atoms to the number of carboxylic acid ester groups or urethane groups in each group R is in the range from 1:20 to 20:1, and
n represents 1 or 2,
or a salt thereof.

DETAILED DESCRIPTION OF PREFERRED EMBODIMENTS

The invention relates to phosphoric acid esters and their salts of the formula (I)

wherein R is an aliphatic, cycloaliphatic and/or aromatic moiety free of Zerewitinoff hydrogen, containing at least one ether oxygen atom (—O—) and at least one carboxylic acid ester group (—COO—) and/or urethane group (—NHCOO—), and having an average molecular weight $\overline{M}$ of 200 to 10,000, in which the hydrogen atoms of the aliphatic groups may be partially replaced by halogen atoms, and wherein the ratio of the number of ether oxygen atoms to the number of the carboxylic acid ester groups and/or urethane groups in each group R is in the range from 1:20 to 20:1, and n is 1 or 2.

The moiety R is an important component of the phosphoric acid esters of the invention. The moiety R preferably represents the residue of an oxalkylated monoalcohol containing carboxylic acid ester groups and/or urethane groups. R particularly preferably represents the residue of a $C_1$–$C_4$ oxalkylated monoalcohol containing carboxylic acid ester groups and/or urethane groups. R most preferably represents the residue of an ethoxylated monoalcohol containing carboxylic acid ester groups and/or urethane groups.

An important feature of the invention is that the phosphoric acid esters contain one or more groups R (which may be the same or different) which contain at least one ether oxygen atom, and at least one carboxylic acid ester group and/or at least one urethane group. These groups produce excellent compatibility with binding agents of paints and molding compositions. It is possible that the groups R may also contain lesser amounts of still other groups containing oxygen and nitrogen, e.g., carboxylic acid amide groups or urea groups. These may arise if the starting alcohols contain another carboxylic acid amide group or an amino group which could react with isocyanate groups. These, however, are more or less only impurities. Basically, not more than one such additional group should be present per R moiety.

In the aliphatic, cycloaliphatic and/or aromatic moiety that contains at least one ether oxygen atom, and at least one carboxylic acid ester group and/or urethane group, and has no Zerewitinoff hydrogen, the ratio of the number of ether oxygen atoms to the number of the carboxylic acid ester groups and/or urethane groups may range from 1:20 to 20:1. Preferably this ratio will range from 1:10 to 10:1, and particularly preferably from 1:5 to 5:1.

The average molecular weight $\overline{M}_n$ of the group R amounts to from 200 to 10,000, preferably from 300 to 5,000, and particularly preferably from 400 to 2,000. This molecular weight can be determined by establishing the molecular weight of the starting materials used in making the compound of Formula I. It can also be determined from the end products, optionally after hydrolytic cleavage of the ROH groups.

A preferred embodiment of the present invention is a phosphoric acid ester in which there is not more than one urethane group in the R moiety per a total of 10 ether oxygen atoms and carboxylic acid ester groups. It is particularly preferred that there be not more than one urethane group per a total of 20 ether oxygen atoms and carboxylic acid ester groups. It is especially preferred that the group R be substantially free of urethane groups.

The invention also relates to the use of the phosphoric acid esters of the invention as dispersants and as dispersion stabilizers, to powdered or fibrous solids for incorporation into liquid systems, which are coated with these phosphoric acid esters as dispersants and/or as dispersion stabilizers. Suitable powdered or fibrous solids are those known in the prior art, especially organic and inorganic pigments, which have been coated with dispersants for use in paints, coatings, molding compositions or other plastics.

A subgroup of such fillers consists of organic and/or inorganic fibers which are used as fillers or reinforcing materials. Examples of suitable pigments and fillers are listed, for example, in European Patent Application No. EP-A 270,126. Additional examples of pigments include diketo-pyrrolo-pyrroles and magnetic pigments formed of mixed oxides of, for example, iron, barium or cobalt or pure iron.

Such powdered or fibrous solids coated with dispersants and dispersion stabilizers according to the invention are prepared in a known manner, for example as described in European Patent Application No. EP-A 270,126, using the phosphoric acid esters of the invention instead of prior art dispersants. In fiber field, such dispersants are often also called sizing agents. The solids can be coated with a solution or emulsion of the phosphoric acid esters, for example in a fluidized bed. The solvent or emulsifying material can then be removed. It can also remain in the mixtures so that pastes are obtained. Another possibility is to suspend the solids in a liquid medium and add the phosphoric acid esters of the invention to this suspension.

Here again the suspension can be produced in such a way that a workable paste is obtained, the liquid medium for forming the suspension being of course adapted to the purpose for which this paste is to be used later on, e.g., adapted to the pigment paste. Such pastes are common commercial products. They can also contain binding resins and/or conventional adjuvants and additives for paints and molding compositions.

There are several possibilities for applying the phosphoric acid esters to the solid surface of pigments, for example, as described in European Patent Application No. EP-A 270,126. This procedure can be performed during or after the synthesis of pigments by adding the phosphoric acid esters to aqueous pigment suspensions, to pigment suspensions in water/solvent mixtures, or to pigment suspensions in solvents, optionally before, during or after a pigment finish, or during their further processing in the application medium.

In comparison to untreated pigments, the pigments according to the invention are distinguished in paints by outstanding rheological properties as well as by clearly improved gloss, viscosity and flocculation properties, and frequently also by greater color strength.

The phosphoric acid esters and their salts according to the invention also can be used—like known prior art dispersants—as dispersants and as dispersion stabilizers by adding the phosphoric acid esters before, during or after formation of a dispersion, to any desired systems, e.g., paints, printing inks, magnetic coatinqs, liquid synthetic resin systems, plastic mixtures and the like, which already contain the solids to be incorporated, such as pigments, fillers or fibers.

Examples of suitable synthetic resins include so-called sheet molding compounds (SMC) or bulk molding compounds (BMC) which comprise unsaturated polyester resins containing reinforcing fibers and fillers. Their preparation and processing is described, for example, in German Patent Application No. DE-A 3,643,007, and in the monograph by P. F. Bruins entitled, "Unsaturated Polyester Technology," Gordon and Breach Science Publishers 1976, pages 211 to 238. To increase the stiffness and improve the surface quality it is generally necessary to add as much filler as possible to these molding compositions. This increases the viscosity of the resin/filler mixtures so sharply that it is no longer possible to achieve proper impregnation of the reinforcing fibers, the release of air is prevented, and the pot life is shortened. By using the phosphoric acid esters of the invention the viscosity of the resin/filler mixtures can be reduced to such an extent that even at very high filler contents, perfect impregnation of the reinforcing fibers is assured.

It is thereby possible to markedly increase the content of fire retardant fillers such as Al(OH)$_3$ and Mg(OH)$_2$, so that the synthetic resin system will have a higher fire retardant rating, and new uses of such plastic materials are facilitated.

The invention also relates to a method of preparing the phosphoric acid esters of the invention and their salts. The phosphoric acid esters of the invention are prepared by reacting one phosphoric acid equivalent of an ester-forming phosphorus compound with one to two equivalents of a compound corresponding to the formula

R—OH wherein R has the meaning described above.

This reaction is described, for example, in U.S. Pat. No. 4,183,766 and in Houben-Weyl, "Methoden der Organischen Chemie," Vol. XII/2, 4th ed., pp. 143 ff. The term, "phosphoric acid equivalent" is understood to refer to that amount of a phosphoric acid compound which upon reaction with a compound of formula R-OH stoichiometrically yields one mole of a compound of Formula I.

If one equivalent of a compound R-OH is used for each phosphoric acid equivalent of an ester-forming phosphorus compound, monoesters form. If two equivalents are used, diesters are formed. If between one and two equivalents are used, a mixture of monoesters and diesters is formed depending on the amount of R-OH that is used.

It is also possible in accordance with the invention for the diesters included in Formula I to contain different R groups. Thus, if the symbol n in Formula I represents the number 2, the R groups can be the same or different. Compounds with different R groups can be made by initially reacting one phosphoric acid equivalent of an ester-forming phosphorus compound with one equivalent of a first compound of formula R-OH in order to make a monoester, and then reacting the monoester with an additional equivalent of a second compound of formula R-OH in which R has a different meaning. It is also possible to react one phosphoric acid equivalent of an ester-forming phosphorus compound with a mixture of various compounds of formula R-OH in which R represents different moieties.

As known to persons skilled in the art, when polyphosphoric acids are used as starting materials in preparing compounds of Formula I, varying amounts of pyro-and polyphosphoric acid monoesters can form as primary products in addition to the phosphoric acid monoesters, especially if an excess of more highly condensed polyphosphoric acids is used (Cf. Houben-Weyl, Vol. XII/2, p. 147). These react with water or moisture, which is often present in powdered solids, to form compounds of Formula I.

As used herein, the term "ester-forming phosphorus compound" is understood to refer to a phosphorus compound which can form a phosphoric acid ester by reaction with a hydroxy compound. For example, phosphorus oxychloride, phosphorus pentoxide, polyphosphoric acid and acetyl phosphate can be used as ester-forming phosphorus compounds. Additional examples are given in German Patent Application No. DE-A 2,726,854. Phosphorus pentoxide and polyphosphoric acid are preferred.

The reaction of the aforementioned ester-forming phosphorus compounds with the monohydroxy compounds is preferably carried out without a solvent, at temperatures up to about 100° C. However, the reaction can also be carried out in the presence of suitable inert solvents, as described, for example, in European Patent Application No. EP-A 193,019.

The resulting phosphoric acid esters are capable of forming salts through their remaining acid groups. They also can be used as dispersants within the scope of the invention in the form of such salts. These salts are obtained from the reaction products of the esterification by neutralization with organic or inorganic bases. Examples of suitable organic bases include primary, secondary and tertiary amines and aminoalcohols as described in U.S. Pat. No. 4,698,099. Examples of suitable inorganic bases include NH$_3$, NaOH, KOH, LiOH, Mg(OH)$_2$ and Ca(OH)$_2$.

The monohydroxy compounds which can be used are those which contain at least one ether oxygen atom (—O—) and at least one carboxylic acid ester group (—COO—) and/or urethane group (—NHCOO—). These are mixed polyether-polyesters, polyether-polyurethanes or polyether-polyester-polyurethanes, and the respective groups can be arranged in blocks or randomly. Block structures are especially suitable because they are easy to prepare and frequently exhibit an especially broad compatibility.

Examples of preferred polyether-polyesters include those obtained by polymerizing a lactone, such as for example propiolactone, valerolactone or caprolactone, substituted derivatives thereof, or mixtures thereof, by means of a monohydroxypolyether starting material. Monoalcohols, advantageously having 1 to 30 carbon atoms, and preferably 1 to 14 carbon atoms, such as methanol, ethanol, propanol, n-butanol, longer-chained saturated and unsaturated alcohols such as oxo alcohols, cyclohexanol, phenylethanol, neopentyl alcohol, and also fluorinated alcohols and substituted and unsubstituted phenols can be used as starting materials for the alkoxylation. Preferred halogen atoms which may be present in the aliphatic groups are fluorine atoms. Such compounds are known to be surface active.

Mixtures of the above-mentioned compounds can also be used. The monohydroxypolyethers advantageously have a molecular weight in the range from about 100 to 5,000.

This lactone polymerization is performed by known methods, such as for example those described in European Patent Application No. EP-A 154,678, initiated, for example, by p-toluenesulfonic acid or dibutyltin dilaurate, at temperatures of about 80° C. to 180° C.

Such hydroxy-functional polyether-polyester blocks can be further alkoxylated in an additional synthesis step using the described methods. The polyether block sequences built up in this way may be the same or different.

Other examples of polyether-polyesters include those which can be obtained by condensation of a glycol and a dibasic acid in the presence of the above-described monohydroxypolyethers. The formation of dihydroxy compounds can be suppressed by using correspondingly stoichiometric amounts of monohydroxypolyethers.

The compounds conventionally used for preparing polyesters in the prior art, such as those mentioned, for example, in German Patent Application No. DE-A 2,726,854, can be used as diols and dibasic carboxylic acids.

If dialcohols which contain ether groups are used, such as for example di-, tri- or polyalkylene glycols, starting alcohols without polyether groups as described, for example, in European Patent Application No. EP-A 154,678, can also be used.

Another example is polyether-polyesters, which are obtainable by condensation of a hydroxycarboxylic acid in the presence of monohydroxypolyethers as described above, for controlling the molecular weight. Polyester-polyethers can also be used, which can be obtained by alkoxylation of a monohydroxy-functional polyester. Suitable polyesters include those which can be obtained by one of the above-described methods in the presence of a monoalcohol. The alkoxylation can be performed by known methods, e.g., with alkylene oxides, ethylene carbonate or propylene carbonate.

The monohydroxy compounds may also be polyether-polyurethanes and/or polyether-polyester-polyurethanes which can be obtained by the addition of a diisocyanate to a dihydroxy compound in the presence of one of the monohydroxy polyethers described above. The reaction occurs according to the following illustrative scheme:

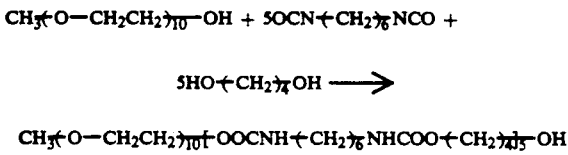

As dihydroxy compounds for forming these urethane group-containing compounds, diols, advantageously those having 2 to 12 carbon atoms, polyoxyalkylene glycols and/or dihydroxy-functional polyesters preferably having molecular weights of at most 2,000, are used as described, for example, in European Patent No. EP-A 270,126 for forming similar compounds.

If dihydroxy compounds which contain ether groups are used, such as, for example, di-, tri- or polyalkylene glycols, then instead of the monohydroxypolyethers, the starting alcohols can be monohydroxy-functional polyesters having preferred molecular weights of no more than 2,000, or other aliphatic, cycloaliphatic and/or aromatic monoalcohols, preferably having 1 to 20 carbon atoms.

As diisocyanates, aliphatic, cycloaliphatic and/or aromatic diisocyanates having 4 to 15 carbon atoms known from polyurethane chemistry can be used, such as for example tetramethylene-, hexamethylene-, trimethylhexamethylene-, dodecamethylene-, isophorone-, toluene- and diphenylmethane diisocyanate, methylene-bis(-4-cyclohexyldiisocyanate), or 1,4-cyclohexane-bis-(methylisocyanate).

By varying the ratio of polyether groups to polyester or polyurethane groups, the compatibility of the phosphoric acid esters can be adapted to the most varied polymeric compounds present in coating and molding compositions in which the phosphoric acid esters according to the invention are used. Thus, for example, compounds of Formula I with a high proportion of polyether groups are especially suitable for aqueous systems.

The invention will be illustrated in further detail by the following, non-limiting examples. For compounds such as polymers in which the molecules are not uniform, the stated molecular weights are numerical average weights ($\overline{M}_n$). The molecular weights or numerical average molecular weights $\overline{M}_n$ can be determined by conventional methods, e.g., by determining the hydroxyl number or the acid number, or cryoscopically. The NCO content of the polyisocyanates which are used, and the progress of the addition reaction, are determined by methods described by Saul Patai, "The Chemistry of Cyanates and their Thioderivates," Part I, Chapter 5, 1977.

Unless otherwise stated in the following preparative examples and use examples, parts refer to parts by weight, and percentages are percentages by weight.

EXAMPLE 1 a) Under a protective atmosphere 503 parts of a nonylphenol ethoxylate having an average molecular weight of 360 were combined with 620 parts caprolactone and 1.12 parts dibutyltin dilaurate and heated to 160° C. The mixture was stirred at this temperature until a solids content of 98% was reached. The resulting polyether-polyester has an average molecular weight of 800.

b) 84.5 parts of thermal polyphosphoric acid with a phosphorus pentoxide content of 84% were added to 800 parts (1 mole) of the monohydroxy compound from step a) and stirred while excluding moisture. After 5 hours of stirring at about 80° C. a phosphoric acid monoester was obtained having an average molecular weight of 880.

EXAMPLE 2

The procedure was the same as described in Example 1, except that instead of polyphosphoric acid, 1 mole of phosphorus pentoxide was used per 3 moles of monohydroxy compound to produce a mono- and diester mixture.

EXAMPLE 3 a) Under a protective atmosphere, 48.3 parts of a decanol-started caprolactone polyester having an average molecular weight of 400 (prepared analogously to Example 1a), 20.2 parts of phthalic acid anhydride, 27 parts of polyethylene glycol ($\overline{M}_n=200$) and 0.3 parts of p-toluene-sulfonic acid were heated to boiling with 52 parts of an aromatic fraction (b.p. 180° C.). The reaction water that formed was removed from the mixture by azeotropic distillation. The reaction ended as soon as no more water could be separated. After distilling off the solvent under reduced pressure, a monohydroxy polyether-polyester was obtained having an average molecular weight of 800.

b) The reaction to the phosphoric acid monoester was performed analogously to Example 1b.

EXAMPLE 4

The monohydroxy compound described in Example 3a was reacted with $P_2O_5$ analogously to Example 2 to form the phosphoric acid mono- and diester mixture.

EXAMPLE 5 a) 71 parts of a nonylphenol ethoxylate having an average molecular weight of 510 were heated with 93.7 parts of isophorone diisocyanate and 0.16 parts of dibutyl tin dilaurate until an exothermic reaction began (about 80° C.). Then 49.3 parts of 2,5-hexanediol were added. The mixture was stirred at the temperature that established itself (about 120° C.) until all of the NCO groups had been reacted. The resulting solid polyether-polyurethane had an average molecular weight of 1540.

b) The reaction to the phosphoric acid monoester was carried out analogously to Example 1b.

EXAMPLE 6

The monohydroxy compound described in Example 5a was reacted with $P_2O_5$ analogously to Example 2 to form the phosphoric acid mono- and diester mixture.

EXAMPLE 7

In a closed apparatus provided with a gas gauge, 66 parts of a decanol-started caprolactone polyester having an average molecular weight of 500 were heated with 75 parts of ethylene carbonate and 0.6 parts of $K_2CO_3$ until the formation of gas began (approximately 190° C.). After the formation of $CO_2$ stopped, a monohydroxy-polyester-polyether was obtained having an average molecular weight of 800.

b) The reaction to the phosphoric acid monoester was carried out analogously to Example 1b.

EXAMPLES 8 to 33

Experiments were run following the procedures of the foregoing examples, except that the starting materials listed in the following Table 1 were used in place of the starting materials of the preceding examples.

TABLE 1

| Example No. | Starting Materials | Moles[1] | $\overline{M}_n$[2] | Method[3] |
|---|---|---|---|---|
| 8 | Tripropyleneglycol monomethyl ether | 1.0 | 800 | 1 |
|   | Caprolactone | 5.2 | | |
| 9 | Tripropyleneglycol monomethyl ether | 1.0 | 500 | 1 |
|   | Caprolactone | 2.7 | | |
| 10 | Dipropyleneglycol monomethyl ether | 1.0 | 500 | 1 |
|   | Caprolactone | 3.0 | | |
| 11 | Ethoxylated $C_{9-11}$ fatty alcohol $\overline{M}_n = 270$ | 1.0 | 800 | 1 |
|   | Caprolactone | 4.7 | | |
| 12 | Ethyl triglycol | 1.0 | 500 | 1 |
|   | Caprolactone | 2.9 | | |
| 13 | Methoxypolyethylene glycol $\overline{M}_n = 350$ | 1.0 | 3000 | 1 |
|   | Caprolactone | 23.3 | | |
| 14 | Methoxypolyethylene glycol $\overline{M}_n = 750$ | 1.0 | 6000 | 1 |
|   | Caprolactone | 46.0 | | |
| 15 | Nonylphenol ethoxylate $\overline{M}_n = 360$ | 1.0 | 1000 | 1 |
|   | Valerolactone | 6.4 | | |
| 16 | Methoxypolyethylene glycol $\overline{M}_n = 750$ | 1.0 | 1500 | 1 |
|   | Valerolactone | 7.5 | | |
| 17 | Tripropyleneglycol monomethyl ether | 1.0 | 800 | 2 |
|   | Caprolactone | 5.2 | | |
| 18 | Dipropyleneglycol monomethyl ether | 1.0 | 500 | 2 |
|   | Caprolactone | 3.0 | | |
| 19 | Ethoxylated $C_{9-11}$ fatty alcohol $\overline{M}_n = 270$ | 1.0 | 800 | 2 |
|   | Caprolactone | 4.7 | | |
| 20 | Methoxypolyethylene glycol $\overline{M}_n = 350$ | 1.0 | 3000 | 2 |
|   | Caprolactone | 23.3 | | |
| 21 | Nonylphenol ethoxylate $\overline{M}_n = 360$ | 1.0 | 1000 | 2 |
|   | Valerolactone | 6.4 | | |
| 22 | Methoxypolyethylene glycol $\overline{M}_n = 750$ | 1.0 | 1500 | 2 |
|   | Valerolactone | 7.5 | | |
| 23 | Phthalic acid anhydride | 2.8 | 800 | 3 |
|   | Dipropylene glycol | 2.8 | | |
| 24 | Decanol-started caprolactone polyester $\overline{M}_n = 400$ | 1.0 | 800 | 3 |
|   | Decane dicarboxylic acid | 2.2 | | |
|   | Dipropylene glycol | 2.2 | | |
| 25 | Decanol-started caprolactone polyester $\overline{M}_n = 400$ | 1.0 | 800 | 3 |
|   | Adipic acid | 2.8 | | |
|   | Dipropylene glycol | 2.8 | | |
| 26 | Decanol-started caprolactone polyester $\overline{M}_n = 400$ | 1.0 | 800 | 4 |
|   | Adipic acid | 2.8 | | |
|   | Dipropylene glycol | 2.8 | | |
| 27 | Methoxypolyethylene glycol $\overline{M}_n = 350$ | 1.0 | 1290 | 4 |
|   | 12-Hydroxystearic acid | 3 | | |
| 28 | Methoxypolyethylene glycol $\overline{M}_n = 350$ | 1.0 | 800 | 3 |
|   | 12-Hydroxystearic acid | 1.5 | | |
| 29 | Methoxypolyethylene glycol $\overline{M}_n = 350$ | 1.0 | 640 | 5 |
|   | Toluene diisocyanate | 1.0 | | |
|   | 1,6-Hexanediol | 1.0 | | |
| 30 | Methoxypolyethylene glycol $\overline{M}_n = 350$ | 1.0 | 770 | 5 |
|   | Isophorone diisocyanate | 1.0 | | |
|   | 1,12-Dodecanediol | 1.0 | | |
| 31 | Methoxypolyethylene glycol $\overline{M}_n = 350$ | 1.0 | 1200 | 5 |
|   | Isophorone diisocyanate | 2.0 | | |
|   | 1,12-Dodecanediol | 2.0 | | |

TABLE 1-continued

| Example No. | Starting Materials | Moles[1] | $\overline{M}_n$[2] | Method[3] |
|---|---|---|---|---|
| 32 | Methoxypolyethylene glycol $\overline{M}_n$ = 350 | 1.0 | 1200 | 6 |
|  | Isophorone diisocyanate | 2.0 |  |  |
|  | 1,12-Dodecanediol | 2.0 |  |  |
| 33 | Ethoxylated C$_{9-11}$ fatty alcohol $\overline{M}_n$ = 530 | 1.0 | 870 | 5 |
|  | Isophorone diisocyanate | 2.0 |  |  |
|  | 1,6-Hexanediol | 2.0 |  |  |

[1] Amount used, in moles
[2] Average molecular weight of the monohydroxy compound obtained in step a)
[3] No. of the example in which the method is described.

As mentioned above, a preferred embodiment of the invention consists in using groups R which do not contain any urethane groups.

If the group —(—O—R)$_n$ in Formula I contains only ester and ether groups, and if in these groups the polyester parts and the polyether parts are in the form of only two blocks, the group R could be represented by the following formula:

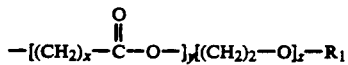

wherein R$_1$ is an alkyl group with 1 to 4 carbon atoms,
x represents an integer from 4 to 5,
y represents a number from 2 to 15, and
z represents a number from 3 to 15.

The above numbers are averages, and may be other than whole numbers, since such polymers always contain mixtures of different compounds corresponding to typical molecular weight distribution curves.

EXAMPLES OF APPLIED USES

Use Example 1

To test the effectiveness of the phosphoric acid esters of the invention, the following mixtures were prepared and their viscosity was measured with a Brookfield Viscosimeter (RVT Spindle 7, 10 rpm):
- 60 parts unsaturated polyester resin solution (acid no. 19-23 mg KOH/g, 68-70% unsaturated polyester resin dissolved in styrene monomer),
- 40 parts polystyrene solution (32-24% polystyrene dissolved in styrene),
- 3.5 parts zinc stearate (lubricant),
- 1.5 parts tertiary butyl perbenzoate,
- 180 parts aluminum hydroxide (e.g. Martinal TM ON 310/Martinal TM OL 104, 2:1)
- 0 and 3.6 parts, respectively, of phosphoric acid esters in accordance with the invention.

The unsaturated polyester resin solution, the polystyrene solution, the tertiary butyl perbenzoate and the phosphoric acid ester of the invention were homogenized in a dissolver, and then the solids, aluminum hydroxide and zinc stearate, were added. After the mixture was allowed to stand for 1 hour at 23° C., the viscosity was measured:

| Phosphoric Acid Ester of the Invention | Viscosity (mPas) |
|---|---|
| — | 621,600 |
| Example 1 | 354,100 |
| Example 12 | 210,000 |
| Example 13 | 225,300 |
| Example 17 | 289,600 |
| Example 21 | 315,200 |
| Example 25 | 387,100 |
| Example 31 | 364,900 |

USE EXAMPLE 2

Mixtures were prepared as in Use Example 1, except having a greater aluminum hydroxide content, and the viscosity of the resin pastes was measured:

| Phosphoric Acid Ester of the Invention (2% based on Al(OH)$_3$) | Aluminum Hydroxide (parts) | Viscosity (mPas) |
|---|---|---|
| — | 180 | 621,600 |
| Example 10 | 250 | 426,300 |
| Example 12 | 250 | 394,200 |
| Example 20 | 250 | 483,700 |
| Example 21 | 250 | 503,900 |
| Example 30 | 250 | 584,900 |
| Example 10 | 260 | 570,700 |
| Example 12 | 260 | 497,600 |
| Example 20 | 260 | 604,800 |
| Example 21 | 260 | 642,400 |
| Example 12 | 270 | 627,000 |

This example clearly shows that the use of the phosphoric acid esters of the invention enables the aluminum hydroxide content to be drastically increased while maintaining or decreasing the original viscosity of the system.

USE EXAMPLE 3

Mixtures of different kinds of thermoplastic components and fillers were prepared, and their viscosities were measured with a Brookfield RVT viscosimeter:
- 70 parts unsaturated polyester resin solution (acid number 25-29 mg KOH/g, 67% unsaturated polyester resin dissolved in styrene),
- 30 parts of styrene-butadiene copolymer solution (30 parts styrene butadiene copolymer dissolved in styrene),
- 1.5 parts tertiary butyl perbenzoate,
- 3.5 parts zinc stearate (lubricant),
- 180 parts CaCO$_3$ (Millicarb TM).

First the liquid components of the above formula were homogenized, and then the zinc stearate and the filler were mixed in. After the mixture had been allowed to stand for one hour at 23° C., the viscosity was measured:

| Phosphoric Acid Ester of the Invention | Parts of Phosphoric Acid Ester | Viscosity (mPas) |
|---|---|---|
| — | — | 282,400 |

-continued

| Phosphoric Acid Ester of the Invention | Parts of Phosphoric Acid Ester | Viscosity (mPas) |
|---|---|---|
| Example 2 | 3.6 | 152,400 |
| Example 12 | 3.6 | 94,000 |
| Example 13 | 3.6 | 105,700 |
| Example 18 | 3.6 | 136,900 |
| Example 21 | 3.6 | 146,100 |
| Example 25 | 3.6 | 162,800 |
| Example 31 | 3.6 | 151,600 |

USE EXAMPLE 4

The following mixtures were prepared in a dissolver:

70 parts unsaturated polyester resin solution (acid no. 25-29 mg KOH/g, 67% unsaturated polyester resin dissolved in styrene)
30 parts styrene-butadiene copolymer solution (30 parts styrene-butadiene copolymer dissolved in styrene),
1.8 parts tertiary butyl perbenzoate,
4.5 parts zinc stearate,
3.5 parts magnesium oxide paste (Luvatol ™ MK 35)(thickener),
3.0 parts styrene,
5.0 parts pigment paste,
220 parts CaCO$_3$,
3.3 parts phosphoric acid ester of Example 21, and 0 parts in the comparative test.

Chopped glass fiber rovings (2.5 cm long) between polyethylene films were impregnated with the mixture on a prepreg apparatus and then allowed to stand for 4 days at 23° C. After removing the cover films the impregnated mass was pressed in a steel mold (40×30 cm) to form pieces 2.0 and 4.0 thick (press pressure 80 bar, mold temperature 150° C. at top, mold temperature 145° C. at bottom, pressing time 2 and 4 minutes, respectively). The glass fiber content was 24%. The pieces had perfect surfaces on which no voids or unwetted glass fiber rovings could be seen. In the experimental attempt to operate without adding the phosphoric acid ester of the invention, it was extremely difficult and tedious to incorporate the same amount of filler into the mixture. Due to its high viscosity, the mixture could not be applied uniformly to the polyethylene films on the prepreg apparatus, and the glass fiber wetting was very inadequate.

USE EXAMPLE 5

A pigment paste was prepared with the phosphoric acid ester obtained in Example 1. 386.5 g of C.I. 1 Pigment White 6 (77.3%), 6.0 g of phosphoric acid ester from Example 1, 88.5 g methoxypropyl acetate and 300 g of glass beads were combined and then dispersed for 20 minutes at 40° C. using a polypropylene disk having a diameter of 40 mm. After filtering out the glass beads, a flowable pigment paste was obtained having excellent rheological properties. By adding 20% of this pigment paste to a clear acrylic melamine varnish (58.1% cross-linking acrylic resin, 14.9% melamine resin, 27% aromatic fraction, b.p.=163-181° C.), and to a clear aldehyde resin varnish (42.8% aldehyde resin, 57.2% xylene), high-gloss enamel films were obtained with perfect surfaces.

If under the same conditions, with the same pigment, a flowable pigment paste was produced without the addition of the phosphoric acid ester, the maximum pigment content which could be achieved was only 42%. If the pigment content was increased, the paste was no longer capable of flowing.

Similar results were obtained with other pigments (in methoxypropyl acetate as solvent):

| Pigment | Pigment content of Paste with Phosphoric Acid Ester | Phosphoric Acid % according to Example 1 | Pigment content without Phosphoric Acid Ester (blank test) |
|---|---|---|---|
| C.I.1 PR 101 | 75.1% | 2.80% | 50.0% |
| Gas black Regular Color Channel | 9.1% | 4.0% | 6.3% |
| C.I. PR 177 | 12.3% | 3.2% | 7.8% |

USE EXAMPLE 6

A salt was produced from the phosphoric acid ester prepared in Example 1 by neutralization with 2-(diethyl-amino)-ethanol. Glass fiber rovings were impregnated with a 5 wt. % aqueous solution of this salt such that after the rovings were dried the phosphoric acid ester content was 0.5 percent of the weight of the glass. Moldings were produced in a press (press pressure 85 bar) at 150° C. from a mixture of 65 parts by weight of the salt treated glass fibers, 35 parts by weight of a 65 weight % unsaturated polyester resin solution in styrene, 3.5 parts by weight zinc stearate, and 1.5 parts by weight tertiary butyl perbenzoate. Measurement of the molded test specimens in accordance with DIN EN 63 showed a flexural strength of 1420 N/mm$^2$ and a flexural modulus of elasticity of 41.6 kN/mm$^2$. Test specimens made under the same conditions from untreated glass fibers showed a flexural strength of only 1250 N/mm$^2$ and a flexural modulus of elasticity of only 39.3 kN/mm$^2$.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all modifications falling within the ambit of the appended claims and equivalents thereof.

What is claimed is:

1. A phosphoric acid ester corresponding to the formula (I)

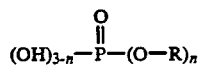

wherein
R represents an aliphatic, cycloaliphatic and/or aromatic moiety free of any Zerewitinoff hydrogen, containing at least one ether oxygen atom (—O—) and at least one carboxylic acid ester group (—COO—) or urethane group (—NHCOO—), and having an average molecular weight $\overline{M}_n$ of 200 to 10,000, wherein aliphatic hydrogen atoms may be partially replaced by halogen atoms, and wherein the ratio of the number of ether oxygen atoms to the number of carboxylic acid ester groups or urethane groups in each group R is in the range from 1:20 to 20:1, and n represents 1 or 2, or a salt thereof; and wherein if R is free of urethane groups, R is terminated at its free end by a monalcohol moiety.

2. A phosphoric acid ester according to claim 1, wherein R represents an oxyalkylated monoalcohol moiety containing at least one group independently selected from the group consisting of carboxylic acid ester groups and urethane groups.

3. A phosphoric acid ester according to claim 1, wherein R represents a ($C_1$–$C_4$)-oxyalkylated monoalcohol moiety containing at least one group independently selected from the group consisting of carboxylic acid ester groups and urethane groups.

4. A phosphoric acid ester according to claim 1, wherein R represents an ethoxylated monoalcohol moiety containing at least one group selected from the group consisting of carboxylic acid ester groups and urethane groups.

5. A phosphoric acid ester according to claim 1, wherein the ratio of the number of the ether oxygen atoms to the total number of carboxylic acid ester groups and urethane groups is in the range from 1:10 to 10:1.

6. A phosphoric acid ester according to claim 5, wherein the ratio of the number of the ether oxygen atoms to the total number of carboxylic acid ester groups and urethane groups is in the range from 1:5 to 5:1.

7. A phosphoric acid ester according to claim 1, wherein R has an average molecular weight $\overline{M}_n$ in the range from 300 to 5,000.

8. A phosphoric acid ester according to claim 7, wherein R has an average molecular weight $\overline{M}_n$ in the range from 400 to 2,000.

9. A phosphoric acid ester according to claim 1, wherein R contains at least 10 total ether oxygen atoms and carboxylic acid groups for each urethane group.

10. A phosphoric acid ester according to claim 1, wherein R is free of urethane groups.

11. A phosphoric acid ester according to claim 10, wherein R corresponds to the formula:

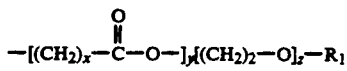

wherein $R_1$ represents an alkyl group with 1 to 4 carbon atoms, x represents an integer from 4 to 5, y represents a number from 2 to 15, and z represents a number from 3 to 15.

12. A phosphoric acid ester according to claim 1, wherein R represents a monohydroxy polyether-polyester formed by reacting an alkanol-started lactone polyester with a dicarboxylic acid or dicarboxylic acid anhydride and a diglycol or polyglycol.

* * * * *